United States Patent
Bodduluri et al.

(10) Patent No.: US 8,986,324 B2
(45) Date of Patent: Mar. 24, 2015

(54) SYSTEMS AND METHODS FOR HARVESTING FOLLICULAR UNITS

(75) Inventors: Mohan Bodduluri, Palo Alto, CA (US); Kyle R. Breton, Fremont, CA (US); Clifford A. Oostman, Jr., Hansville, WA (US); George D. Hermann, Portola Valley, CA (US)

(73) Assignee: Restoration Robotics, Inc., San Jose, CA (US)

( * ) Notice: Subject to any disclaimer, the term of this patent is extended or adjusted under 35 U.S.C. 154(b) by 401 days.

(21) Appl. No.: 12/855,916

(22) Filed: Aug. 13, 2010

(65) Prior Publication Data
US 2012/0041451 A1    Feb. 16, 2012

(51) Int. Cl.
| | |
|---|---|
| *A61B 17/32* | (2006.01) |
| *A61B 17/34* | (2006.01) |
| *A61B 17/3205* | (2006.01) |
| *A61B 17/00* | (2006.01) |

(52) U.S. Cl.
CPC ....... *A61B 17/32053* (2013.01); *A61B 17/3468* (2013.01); *A61B 2017/00752* (2013.01)
USPC ............ 606/133; 606/184; 606/185; 606/187

(58) Field of Classification Search
CPC ................... A61B 17/32002; A61B 17/32053; A61B 2017/00353; A61B 2017/00752; A61B 19/2203
USPC ........... 606/51, 133, 167, 170, 171, 184, 185; 600/564–568; 604/93.01, 156
See application file for complete search history.

(56) References Cited

U.S. PATENT DOCUMENTS

| | | |
|---|---|---|
| 3,998,230 A | 12/1976 | Miller |
| 4,160,453 A | 7/1979 | Miller |
| 4,785,826 A | 11/1988 | Ward |
| 5,423,330 A | 6/1995 | Lee |
| 5,573,008 A | 11/1996 | Robinson et al. |
| 5,584,841 A | 12/1996 | Rassman |
| 5,693,064 A | 12/1997 | Arnold |
| 5,817,120 A | 10/1998 | Rassman |

(Continued)

FOREIGN PATENT DOCUMENTS

| | | |
|---|---|---|
| WO | 2008/027829 | 3/2008 |
| WO | WO 2008/115526 | 9/2008 |
| WO | 2009/017445 | 2/2009 |

OTHER PUBLICATIONS

Harris, James A. MD, FACS: "New Methodology and Instrumentation for Follicular Unit Extraction: Lower Follicle Transection Rates and Expanded Patient Candidacy", 2006. American Society for Dermatology Surgery, Inc.

(Continued)

*Primary Examiner* — Kathleen Holwerda
*Assistant Examiner* — Sarah W Aleman
(74) *Attorney, Agent, or Firm* — Sharon Upham; Lena I. Vinitskaya (57) ABSTRACT

Systems and methods are provided for harvesting hair grafts from a body surface utilizing a removal tool comprising first and second elongated bodies. The described systems and methods serve to eliminate and/or at least minimize unnecessary compression of adjacent tissue during the removal process, thereby minimizing damage to the follicular unit being removed, reducing the opportunities for the follicular unit to intersect the path of the harvesting tool, and/or improving the quality of the removed specimen, preferably preserving its integrity.

30 Claims, 3 Drawing Sheets

(56) References Cited

U.S. PATENT DOCUMENTS

| | | | |
|---|---|---|---|
| 5,885,226 | A | 3/1999 | Rubinstein et al. |
| 6,059,807 | A | 5/2000 | Boudjema |
| 6,086,543 | A | 7/2000 | Anderson et al. |
| 6,142,955 | A | 11/2000 | Farascioni et al. |
| 6,273,861 | B1 | 8/2001 | Bates et al. |
| 6,306,142 | B1 | 10/2001 | Johanson et al. |
| 6,402,701 | B1 | 6/2002 | Kaplan et al. |
| 6,585,746 | B2 | 7/2003 | Gildenberg |
| 7,144,406 | B2 * | 12/2006 | Pak et al. ............... 606/187 |
| 7,156,856 | B2 | 1/2007 | Feller |
| 7,172,604 | B2 | 2/2007 | Cole |
| 7,364,540 | B1 | 4/2008 | Burton et al. |
| 2001/0031941 | A1 | 10/2001 | Edwards et al. |
| 2004/0024349 | A1 | 2/2004 | Flock et al. |
| 2004/0102730 | A1 | 5/2004 | Davis et al. |
| 2004/0162505 | A1 * | 8/2004 | Kaplan et al. ............ 606/167 |
| 2004/0193203 | A1 | 9/2004 | Pak et al. |
| 2005/0085838 | A1 | 4/2005 | Thompson et al. |
| 2005/0267506 | A1 | 12/2005 | Harris |
| 2006/0161179 | A1 | 7/2006 | Kachenmeister |
| 2007/0078473 | A1 * | 4/2007 | Bodduluri et al. ......... 606/167 |
| 2007/0156164 | A1 | 7/2007 | Cole |
| 2008/0234698 | A1 * | 9/2008 | Oostman et al. ........... 606/133 |
| 2008/0234699 | A1 | 9/2008 | Oostman et al. |
| 2010/0030234 | A1 | 2/2010 | Bodduluri et al. |
| 2010/0125287 | A1 | 5/2010 | Cole et al. |
| 2011/0224693 | A1 | 9/2011 | Bodduluri et al. |

OTHER PUBLICATIONS

Inaba, M. and Inaba, Y.: "Androgenetic Alopecia, Modern Concepts of Pathogenesis and Treatment, 29. Operative Treatment for Androgenetic Alopecia". 1996. Springer, pp. 238-244, 309.

Teresa Riordan: "Patents: Implanting hair is tedious, exacting work—the perfect work for a robot". New York Times. Sep. 15, 2003.

Bernstein, Robert M.; Rassman, William R.: "New Instrumentation for Three-Step Follicular Unit Extraction". Hair Transplant Forum International (Official publication of the International Society of Hair Restoration Surgery) vol. 16, No. 1, Jan./Feb. 2006. (4 pages).

PCT Int'; Search Report and Written Opinion for commonly assigned PCT/US2011/047680, Forms PCT/ISA/220, PCT/ISA/210 and PCT/ISA/237. Applicant Restoration Robotics, Inc., dated Mar. 27, 2012 (17 pages).

Extended European Search Report, mailed Mar. 11, 2014, in connection with commonly assigned European Application No. 11817155.2 (7 pages).

* cited by examiner

SYSTEMS AND METHODS FOR HARVESTING FOLLICULAR UNITS

FIELD OF THE INVENTION

The present application relates generally to methods used for the harvesting of follicular units from a body surface.

BACKGROUND OF THE INVENTION

Hair transplantation procedures are well-known, and typically involve harvesting donor hair grafts from a patient's scalp, and implanting them in a bald area ("recipient area"). In one well-known process, singular follicular units are harvested utilizing a hollow needle punch having a cutting edge and an interior lumen with a diameter, for example, of 1 mm. The needle punch is axially aligned with an axis of a follicular unit to be extracted and then advanced into the scalp to cut the scalp about the circumference of the selected follicular unit. Thereafter, the follicular units are removed, e.g., using forceps, for subsequent implantation into a recipient site with a specially devised insertion needle.

Automated hair transplantation systems utilizing a robot, including a robotic arm and a hair follicle introducer associated with the robotic arm are also known.

SUMMARY OF THE INVENTION

In accordance with one general aspect, the present application discloses a method of harvesting a follicular unit, the method comprising the step of advancing the harvesting cannula (e.g. comprising a single elongated body) into the body surface in a series of one or more advancing and retracting steps, until the distal end of the harvesting cannula is disposed at a depth in the body surface sufficient to encapsulate a follicular unit. The advancing and retracting steps may be performed in a pulsed manner having a variety of constant and/or varying advancing and retracting increments.

In accordance with another aspect, the present application discloses a method of dissecting a follicular unit using a multi-part tool assembly comprising coaxially disposed first and second elongated bodies. This method comprises advancing a first elongated body relative to a skin surface such that a distal tip of the first elongated body penetrates the skin surface surrounding a follicular unit and initiates a path; advancing the second elongated body relative to the skin surface, such that a distal tip of the second elongated body enters the skin surface following the path initiated by the first elongated body, the distal tip of the second elongated body being duller than the distal tip of the first elongated body; and wherein while beneath the skin surface the second elongated body is advanced in a pulsed manner, the pulsed manner comprising a succession of advancing and retracting steps, for example, in an alternating manner. In some embodiments, advancement of the second elongated body in the pulsed manner begins after the second elongated body has reached a first depth beneath the skin surface. Such depth, for example, may be the same or deeper than a depth that the first elongated body penetrates beneath the skin surface.

In another embodiment a method of harvesting follicular units using a multi-part tool assembly is provided. The tool assembly comprising coaxially disposed first and second elongated bodies, the second elongated body configured to receive a follicular unit in a lumen thereof, the method comprising: advancing the first elongated body relative to the skin surface such that a distal end of the first elongated body penetrates the skin surface surrounding a follicular unit to initiate a path penetrating to a first depth; advancing the second elongated body relative to the first elongated body such that a distal tip of the second elongated body enters the body surface and follows the path initiated by the first elongated body, the distal tip of the second elongated body being duller than the distal tip of the first elongated body; withdrawing the first elongated body from the skin surface; advancing the second elongated body further into the body surface in a series of two or more advancing and retracting steps, until the distal end of the second elongated is disposed at a second depth in the skin surface and encapsulates the follicular unit; and withdrawing the second elongated body, from the skin surface.

Yet another method of dissecting a follicular unit using a multi-part tool assembly comprising coaxially disposed first and second elongated bodies is provided. The method comprises: advancing a first elongated body relative to a skin surface such that a distal tip of the first elongated body penetrates the skin surface surrounding a follicular unit and initiates a path penetrating to a first depth; advancing the second elongated body relative to the skin surface, such that a relatively duller distal tip of the second elongated body enters the skin surface following the path initiated by the first elongated body and wherein while beneath the skin surface the second elongated body is advanced in a succession of advancing steps. The advancing steps may include advancing the distal tip of the second elongated body to an intermediate depth and maintaining it at the intermediate depth for a predetermined time to allow the follicular unit at least partially recover from its compressed state and then advancing to a second depth at which the follicular unit is substantially dissected.

According to another aspect, in certain embodiments, methods of dissecting and/or harvesting follicular units comprise utilizing a pulsed vacuum during the harvesting process, the pulsed vacuum is applied while the harvesting cannula is beneath the body surface. In one example, the elongated body of the harvesting tool is advanced relative to the skin surface such that a distal end of the elongated body enters the skin surface surrounding a follicular unit. A source of pressure differential (which, for example, may be in communication with a proximal end of a lumen of the elongated body) is applied and provides an alternating elevated and less elevated pressure differential within the lumen of the elongated body to assist in harvesting of the follicular unit. Application of such "pulsed" pressure differential or vacuum as the harvesting cannula or elongated body enters the body or skin surface, may cause the follicular unit to be elongated during the provision of elevated pressure and allow the follicular unit to relax during a less elevated pressure setting. The pulsed pressure differential or vacuum may be terminated once the follicular unit has been dissected from the surrounding tissue, or may continue as additional measures are taken to extract the dissected follicular unit from the body surface.

In certain embodiments, a system and a method of dissecting follicular units using a bifurcated follicular unit removal tool is provided. The tool may comprise coaxially disposed first and second elongated bodies, the second elongated body having a primary lumen in communication with a larger secondary lumen (e.g., through an opening). For example, a secondary lumen may divert from the primary lumen at an angle. The first elongated body may have a sharp distal tip for piercing the skin, while the second elongated body may have a distal tip that is dull or less sharp than the distal tip of the first elongated body. The system may further comprise a source of pressure differential in communication with the secondary lumen of the second elongated body. The method comprises advancing the first elongated body relative to a skin surface such that a distal tip of the first elongated body penetrates the skin surface surrounding a follicular unit to initiate a path; advancing the second elongated body relative to the first elongated body such that a distal tip of the second elongated body enters the body surface and follows the path initiated by the first elongated body; withdrawing the first elongated body (e.g. through the primary lumen of the second elongated body) such that the distal tip of the first elongated body substantially clears the opening between the primary and the secondary lumen of the second elongated body. The method may also comprise directing a follicular unit into a larger secondary lumen of the second elongated body, for example, by activating a source of pressure differential to provide a pressure differential within the secondary lumen of the second elongated body urging the follicular unit to propagate in the direction of the secondary lumen. The pressure differential may comprise an alternating elevated and a less elevated pressure. In certain embodiments, the vacuum or pulsed vacuum may be applied to the secondary lumen. The above bifurcated harvesting tool and corresponding method may be incorporated into various follicular unit harvesting procedures.

Other and further objects and advantages of the invention will become apparent from the following detailed description when read in view of the accompanying figures.

BRIEF DESCRIPTION OF THE DRAWINGS

It should be noted that the drawings are not to scale and are intended only as an aid in conjunction with the explanations in the following detailed description. Features and advantages of the present invention will become appreciated as the same become better understood with reference to the specification, claims, and appended drawings wherein:

DETAILED DESCRIPTION OF THE PREFERRED EMBODIMENTS

In the following Detailed Description, reference is made to the accompanying drawings that show by way of illustration some exemplary embodiments in which the invention may be practiced. In this regard, directional terminology, such as "distal," "proximal," "inner," "outer," "upwards," "downwards," "advancing," "withdrawing," etc., are used with reference to the orientation of the Figure(s) being described. Because components or embodiments of the present invention can be positioned in a number of different orientations, the directional terminology is used for purposes of illustration and is in no way limiting. It is to be understood that other embodiments may be utilized and structural or logical changes may be made without departing from the scope of the present invention. The following description, therefore, is not to be taken in a limiting sense, and the scope of the present invention is defined by the appended claims.

The term "tool," or "harvesting or removal tool," or "follicular unit removal tool" as used herein refers to any number of tools or end effectors that are capable of removing or harvesting follicular units ("FUs") from a body surface. A body surface can be attached to the body or may be a flap of skin or body tissue removed from the body. Such tools may have many different forms and configurations. In many embodiments, the tool comprises a hollow tubular shaft and thus may be labeled, for example, a cannula, a needle, or a punch. The distal end of removal tools (for example, punches, coring devices, cutting and/or trimming devices, needles), are typically sharpened, to various degrees, to cut and extract the follicular unit.

The various embodiments of the methods of the present application are useful in manual procedures and systems, as well as in fully- or semi-automated procedures and systems. The automated systems may also be robotically-assisted or computer, software, and/or machine-instruction controlled. The tools of the current application can also be used with the robotically-assisted systems and procedures and they could be configured for use with those robotic systems, for example, as described in the commonly-assigned US Patent Publication No. 2007/0106306 and US Patent Publication No. 2008/0234699, the disclosure of both applications is incorporated herein by reference.

Embodiments of the methods of the present invention may be implemented using computer software, firmware or hardware. Various programming languages and operating systems may be used to implement the present invention.

It has been found that the actual process of advancing a punch, needle or similar device into the scalp to harvest a follicular unit, whether it is manually or automatically, may cause certain problems to arise. Generally hair follicles have a hair shaft extending, for example, through the epidermis, dermis and subcutaneous fat layers of the skin. They also have a hair bulb (a subsurface bottom-most portion) which represents one of the critical structures of the follicle that contain follicular stein cells and melanocytes. In addition, other critical structures containing stein cells include, for example, sebaceous glands and outer root sheath. When harvesting follicular units for subsequent implantation in another area, it is important not to damage these critical structures, for example, by transecting (cutting off) with the harvesting tool these important structures of the hair follicle. The hair follicles do not usually maintain the same direction or angle of growth under the skin surface as above the skin surface. Therefore, advancing the harvesting tool under the skin surface in reliance on the direction of the hair follicle above the skin surface, often results in follicular unit transection. In the case of a sharp punch or needle being used, if the sharp punch penetrates too deeply into the body surface, there is an increased chance that the follicular unit will be transected, thereby damaging it or rendering it unusable.

Furthermore, even though the user may initiate the harvesting process when the hair is in a relaxed hair state, as the punch or needle used to remove the follicular unit is pushed into a body surface surrounding the follicular unit, the downward pressure depresses the body surface in the vicinity of the punch needle, and propagates through the tissue adjacent the follicular unit, sometimes causing tissue compression, and/or the follicular unit to be deformed, alter in location and/or orientation. For example, the ends of the follicular unit proximal the body surface may be urged in a direction closer to the skin or body surface, and/or parts of the follicular unit within the body surface may be temporarily deformed such that certain parts of the follicular unit are pushed either into the path of the distal end of the punch needle, that were not previously in its path. This temporary deformation increasing the chance of transection during the harvesting process, and thus reducing the chances of a successful transplantation. This ultimately reduces the yield and increases the time for the entire transplantation process.

According to the various embodiments described herein, a variety of systems and methods utilizing a follicular unit removal tool were developed which serve to reduce, and/or minimize unnecessary compression of adjacent tissue during the removal process, thereby minimizing damage to the follicular unit being removed, reducing the opportunities for the follicular unit to intersect the path of the harvesting tool, and/or improving the quality of the removed specimen, preferably preserving its integrity. These systems and methods may also serve to reduce the transection rate of follicular units during the dissection process. These systems and methods can be incorporated into the use of manual tools, motorized powered instruments, as part of an automated or semi-automated system, and/or of part of a computer or robotically controlled system.

Figure 1A:
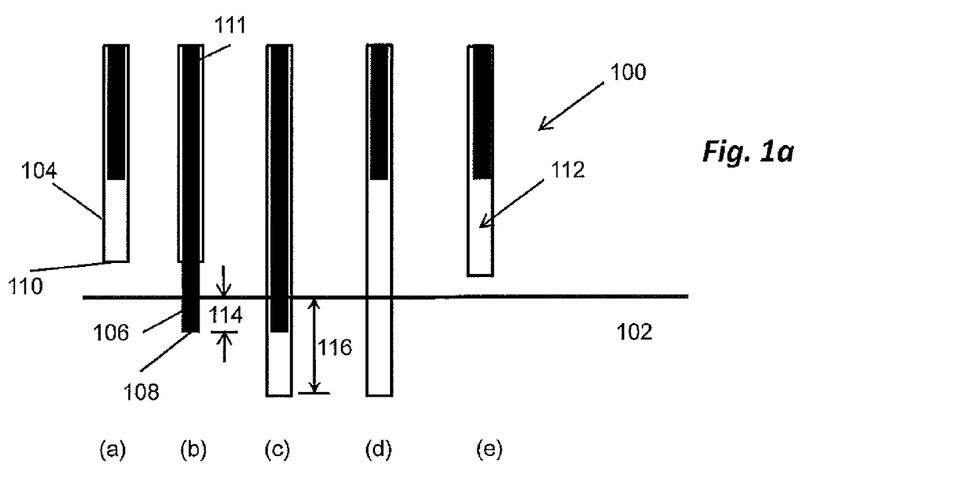
FIG. 1a illustrates the stages of operation of an example of an embodiment of the invention, directed to blowback.

FIG. 1a shows a follicular unit removal tool 100 operating through various stages according to an embodiment of a method to remove or harvest a follicular unit (not shown) from a donor area such as a scalp or other body or skin surface 102 containing hair. The reader is advised that the focus of the illustrated method is on the distal end of the features discussed, and that the proximal end may be configured to suit any particular need. For example, there are various ways in which the elongated bodies can be maneuvered. For example, the removal tool 100 may be configured to incorporate a handle and/or appropriate sleeves, slidable shafts, or other such structures to move the elongated bodies, for example, axially and/or radially relative to one another. In an alternative configuration, the proximal end of the removal tool 100 may be adapted to enable one or more of a mechanical system, electromechanical system, a pneumatic system, hydraulic system, or a magnetic system for effecting controlled movement of the first and second elongated bodies relative to one another, and to facilitate a semi- or fully-automated tool to be employed. In yet another alternative configuration, either or both of the elongated bodies may be operatively coupled to a biasing mechanism, such as a spring mechanism, or other such release mechanism to facilitate movement of the elongated body in the axial direction, in a quick, or slow or otherwise controlled manner. In yet a further alternative configuration, the removal tool can be implemented in a robotically-assisted system, such as that described in the U.S. Publication Nos. 2007/0106306 and 2008/0234699 already incorporated by reference herein. In this particular embodiment the removal tool may be connected directly or indirectly to an automated (e.g., robotic) arm, so that movement of the removal tool relative to the body surface may be performed by either movement of the robotic arm relative to the body surface, or movement of the removal tool relative to the automated arm, or a combination of each.

Figure 1B:
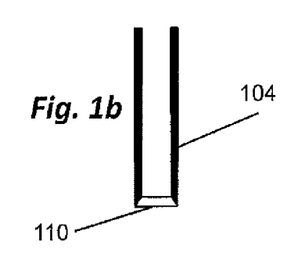
FIGS. 1b and 1c illustrate alternative distal ends of the elongated bodies.

In reference to FIG. 1a, the removal tool 100 may include a first elongated body 106 and a second elongated body 104, which may be substantially coaxially disposed relative to each other. In this particular example, the first elongated body 106 comprises a sharp distal tip 108, although in other embodiments it may have various degrees of sharpness, including being relatively "dull". The term "sharp" distal tip 108 as used herein means that it is sharp enough to pierce or cut a skin or body surface 102. The distal tip 110 of the second elongated body 104 is less sharp than the sharp distal tip 108 of the first elongated body 106. The distal ends of the elongated bodies 104, 106, including distal tips 108, 110 may comprise tapers or bevels, as illustrated in FIG. 1b. The tapers may be configured in different ways, for example, by decreasing overall dimensions of the elongated members at their distal ends, decreasing one side in preference to another, or by any other means known in the ad. In different embodiments, one of the elongated bodies, for example, the second elongated body 104 could be either an inner or an outer elongated body relative to the first elongated body 106. In the example of FIG. 1a, the second elongated body 104 is shown as an outer elongated body. The dimensions and internal shape of the second elongated body 104 is configured such that it is capable of at least partially surrounding or encapsulating a follicular unit within its lumen 112. The dimensions and internal shape of the first elongated body 106 may be also configured such that it is capable of at least partially surrounding or encapsulating a follicular unit within its lumen 111. One or both of the first and second elongated bodies 106, 104 may be axially movable relative to one another, and optionally radially movable relative to one another.

Figure 1C:
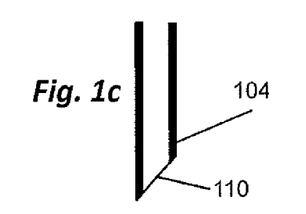

Although the distal tips 108, 110 of the elongated bodies 104, 106 in FIG. 1a are illustrated as being "straight", or being substantially perpendicular to the longitudinal axis of the elongated bodies 104, 106, the distal tips 108, 110 may be angled, as illustrated in FIG. 1c. While it is known to angle or slant the sharp piercing distal tips of the tools and cannulas used for cutting and piercing tissue, it was discovered by the inventors of the present application that angling a relatively dull distal end, for example, of the second elongated body 104 provides certain advantages, such as reduces chances of transection of the hair follicles, especially when the elongated body 104 is advanced to deeper levels to surround the lower portion of the follicular unit or hair graft under the skin surface. By angling the distal tip, rather than having a leading circular periphery, there is a projecting or leading portion of the distal tip, and the distal peripheral edge is typically oval in shape. As the second elongated body 104 with the relatively dull distal tip may generally enter the incision already created by the more sharp distal tip 108 of the second elongated body 106, it is able to move through the tissue and dissect the follicular unit without the need for a sharp edge. Thus, as the elongated body penetrates the skin and moves deeper through the skin layers, since the distal tip is relatively dull and angled, its leading portion is more gentle on the follicular unit and surrounding tissue, and the rest of the distal peripheral edge follows with minimal damage. Moreover, in certain embodiments, it is beneficial to rotate the angled distal tip of the elongated body as it penetrates the skin to dissect hair graft. The angled nature of the distal tip being forgiving to tissue at points other than those that intersect directly with the leading edge while rotation allows for improved dissection all around the follicular unit while minimizing damage to it. The utilization of an angled dull distal tip 110 that is rotated as it enters the body surface 102 may further reduce the chances of transection.

One embodiment of the method of harvesting follicular units will be described now in reference to FIG. 1a. Step (a) shows the distal end portion of the removal tool 100 disposed above the skin or body surface and in proximity to a follicular unit to be harvested (not shown) from a body surface 102. The first elongated body 106 is in its retracted position, the sharp distal tip 108 of the first elongated body 106 is retracted inside the lumen 112 of the second elongated body 104. In this position, the sharp distal tip 108 of the first elongated body 106 is also protected from contamination or any other such damage from external elements. The user is likewise protected from unintentional puncturing of his/her skin by merely handling the tool. In step (b), the sharp distal tip 108 of the first elongated body 106 is moved or thrust axially, for example, at a relatively high speed to pierce the body surface 102 to cut or incise tissue, or skin layers, to a desired depth (e.g. through the epidermis, or upper dermis) for example to a depth 114 of approximately 1 to 2 mm.

Subsequently, in step (c) the second elongated body 104 advances, in this embodiment, over the first elongated body 106, such that the distal tip 110 of the second elongated body 104 enters the body surface 102, following the path initiated by the first elongated body 106. The second elongated body advances deeper than the depth 114 (e.g. 1 to 2 mm) reached by the sharp distal tip 108, to a second depth 116 such that the distal end of the second elongated body 104 encapsulates the follicular unit in its lumen 112. At this point, in step (d) the first elongated body 106 is "blown back" or retracted, such as into the second elongated body 104, thereby providing more space in the lumen 112 of the second elongated body 104 for the follicular unit to expand into, and consequently reduce the pressure to which the tissue surrounding the follicular unit is subjected. Although in step (c) the illustration shows that the second elongated body reaches its second depth 116 before the first elongated body 106 is retracted or "blown back", it will be noted that the first elongated body 106 may be retracted earlier in the process, for example, any time during advancement of the second elongated body 104 under the skin surface, preferably at a point when the distal tip 110 of the second elongated body 104 is disposed at or between the first and second depths 114 and 116 respectively. This earlier retraction may aid in reducing transection, by allowing the compressed tissue that surrounds the follicular unit to expand and/or at least partially return to its non-compressed state, allowing the hair(s) in the follicular unit to be less deformed by the force to which the tissue was exposed, and hopefully also reduces the opportunity for transection. According to the novel technique described above, at least some parts of the follicular unit within the body surface are therefore in a somewhat more relaxed or less compressed tissue medium than that of the previously existing hair harvesting techniques.

The concentric elongated body configuration of the removal tool described above relies on the formation of an incision made by the sharp distal tip 108 of the first elongated body 106 after which the less sharp distal tip 110 of the second elongated body 104 follows into the tissue of the body surface 102. One undesirable possibility is the enlargement or destruction of the clean incision by the blunt distal tip 110 of the second elongated body 104. To help prevent such damage, the second elongated body 104 may be rotated while the descending into the incision to reduce the chance of catching on the incision from direct linear movement. Alternatively, a small annular space between the first and second elongated bodies may be designed so that the second elongated body 104 rotates slightly off the axis of the first elongated body 106 so as to wobble or be mis-aligned with respect thereto. For that matter, both elongated bodies 104, 106 might be caused to rotate off-center from their own axes and wobble. The wobbling from one or both elongated bodies may allow the outside elongated body to spiral into the opening created by the inside elongated body. In yet another alternative, the relatively dull distal tip 110 of the second elongated body 104 could be angled, as described earlier.

Having dissected the follicular unit from the surrounding tissue, in a final step (e), the elongated body 104 is withdrawn from the body or skin surface 102. Depending on the specific design and application, and depending on the desirable precise order of withdrawal of the second and first elongated bodies from the skin, the removal tool may be withdrawn with the follicular unit in the lumen 112. In other embodiments, the removal tool may be removed while a dissected follicular unit may remain in the body surface, and then subsequently removed, for example, with the additional assistance of forceps, or other appropriate tools or mechanisms. Alternatively, a retention member (not shown) may be incorporated into the second and/or first elongated bodies to assist with the removal of the graft.

Another method for removing or assisting in removal of the follicular unit from the body surface 102 may utilize suction. Suction may be applied such that a pressure differential is created within a lumen 112 of the second elongated body, such that when applied, the follicular unit is urged to move in a proximal direction, that is, out of the body surface. It was discovered that it may be beneficial to pulse the pressure applied during the time follicular unit is being removed from the skin and urged during its movement along at least a part of the lumen of the removal tool. For example, the system may be configured such that the pulsed differential pressure may be applied between steps (c) and 1(e), for example. Having taken various steps to minimize the trauma, pressure, or damage transmitted to the incised follicular unit, this pulsed vacuum may be beneficial in also minimizing the damage on the now dissected follicular unit. In addition, this "vacuum pulsing" technique described in more detail below may also serve to assist in the removal or separation of follicular units which may be tethered to the tissue at the base thereof while reducing or eliminating potential damage to the follicular unit. For example, the methods of harvesting hair grafts may include pulsing the vacuum pressure between a maximum vacuum pressure value (elevated pressure) and atmospheric pressure (less elevated pressure) using a pulsing period, for example, of about 0.25 to 1 second. During the pulsing cycle, the follicular unit may be elongated during maximum vacuum stretching in a direction out of the body surface 102, and then allowing the follicular unit to relax during, for example, an atmosphere pressure. By repeating this stretching and relaxation technique, the follicular unit may effectively "worm" its way into and up the lumen 112 of the second elongated body 104. Application of a pulsed differential pressure or vacuum assists in removing the follicular unit out of the body surface 102 while decreasing a chance of follicular damage, for example, by avoiding the follicular unit being torn at the base. The harvesting systems of any of the embodiments that implement pulsed vacuum, may comprise a controller that regulates vacuum pulsing during advancement of the elongated body(s).

Figure 2:
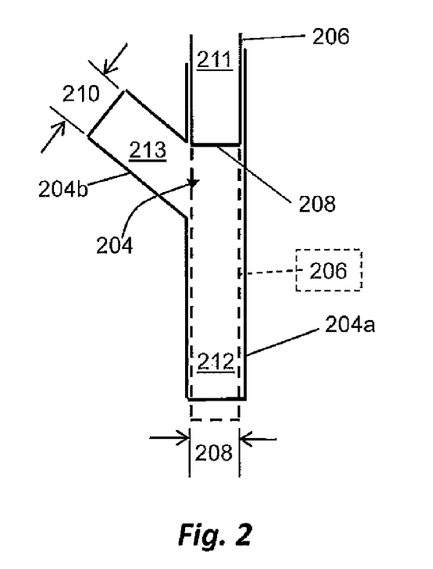
FIG. 2 illustrates an example of an embodiment of the invention incorporating a bifurcated structure of a follicular unit removal tool.

FIG. 2 illustrates another embodiment of a removal tool and corresponding method that solves another issue associated with some of the existing harvesting devices: it improves conditions of passage of the follicular unit through the harvesting cannula or cannulas while reducing damage to the graft. It has been observed that the configuration of existing follicular unit removal tools is such that having disconnected the follicular unit from the body surface, the follicular unit has to travel in an upwards direction in a generally narrow lumen of the harvesting cannula (which narrows even further if the harvesting tool has an inner cannula inside the lumen of the outer cannula). In addition to the difficulty of effective and speedy removal of the follicular unit or hair graft, as well as a possibility of it being stuck inside the lumen, during this journey, at least a portion of the tissue surrounding the follicular unit may be potentially exposed to the sharp distal tip of the inner cannula. The embodiment described below addresses this issue.

In FIG. 2, the first elongated body 206 with its sharp distal tip 208 may be similar to that of the embodiment described with respect to FIG. 1a. However, in this configuration, the second elongated body 204 comprises a bifurcated or Y-shaped structure. The first section 204a of the bifurcated structure comprises a lumen 212 and corresponds to the second elongated body 104 illustrated in FIG. 1a, but the second section 204b of the second elongated body 204 diverts at an angle from the primary path or lumen 212 of the first section 204a and forms a secondary connected path or lumen 213. The lumens may be connected, for example, through an opening. The lumen 213 has a greater capacity, for example a greater cross-sectional area than that of the lumen 211 of the first elongated body 206. Lumen 213 may also have a cross-sectional area equal to or greater than the cross-sectional area of lumen 212

In operation of this particular configuration, steps (a) through (d) may be the same as described above, but an additional step is carried out between steps (d) and 1(e). As described above in step (d) the first elongated body 206 may be "blown back" or retracted into the first section 204a of the elongated body 204, thereby providing more space in the lumen 212 of the second elongated body 204 for the follicular unit to expand into, and consequently reduce the pressure to which the tissue surrounding the follicular unit is subjected. The first elongated body 206 is withdrawn or retracted back far enough to ensure the opening to the lumen 213 is substantially clear. Having allowed the follicular unit to decompress, rather than require the same follicular unit to squeeze into the lumen 211 of the first elongated body 206, in order to improve and/or speed up the movement of the follicular unit through the removal tool, an alternative route for the follicular unit is provided. The route is through the larger capacity lumen 213 of the second section 204b of the second elongated body 204. For example the inner diameter of lumen 211 may be approximately 1.0 mm, whereas the inner diameter of lumen 213 may be 1.3 mm or greater. This configuration is especially useful in combination with suction that may be applied such that a pressure differential is created within a lumen 213. When suction is applied through a lumen 213, the follicular unit is urged to move out of the body surface 102 but in the direction of the larger lumen 213, thereby improving the speed of removal and possibly avoiding damage to the follicular unit. Optionally, a pulsed pressure differential may be applied, varying the pressure applied to remove the follicular unit. By so doing trauma, pressure, or damage transmitted to the dissected follicular unit, is minimized for the dissected follicular unit. Generally, the method associated with the bifurcated follicular unit removal tool of FIG. 2 comprises advancing the first elongated body relative to a skin surface such that a distal tip of the first elongated body penetrates the skin surface surrounding a follicular unit to initiate a path; advancing the second elongated body relative to the first elongated body such that a distal tip of the second elongated body enters the body surface and follows the path initiated by the first elongated body; withdrawing the first elongated body such that the distal tip of the first elongated body substantially clears an opening between a primary and a larger secondary lumen of the second elongated body; and directing a follicular unit into a larger secondary lumen of the second elongated body. The method may comprise activating a source of pressure differential to provide a pressure differential within the secondary lumen of the second elongated body urging a follicular unit to propagate in the direction of the secondary lumen. In FIG. 2, the angle between the axis of lumen 212 and the axis of lumen 213 is shown to be approximately 45 degrees. However, other angles may be used, such as more gradual or acute angles (e.g. 15 to 45 degrees). In the embodiments with more gradual angle between the two lumens, it is easier for the follicular unit to be redirected into the alternate lumen. More gradual angles subject the follicular unit to less bending and other trauma as it is redirected. Also the open area at the junction of the two lumens is larger with narrower angles, thus providing a greater surface area for the vacuum (pressure differential) to be exerted on the follicular unit as it is redirected. It will be appreciated that the above-mentioned removal tool with a bifurcated structure, and the methodology associated therewith may be implemented not only in conjunction with the method of FIG. 1a, or other methods described in this application, but may also be beneficial when implemented in conjunction with other known methods of hair harvesting for transplantation.

Figure 3:
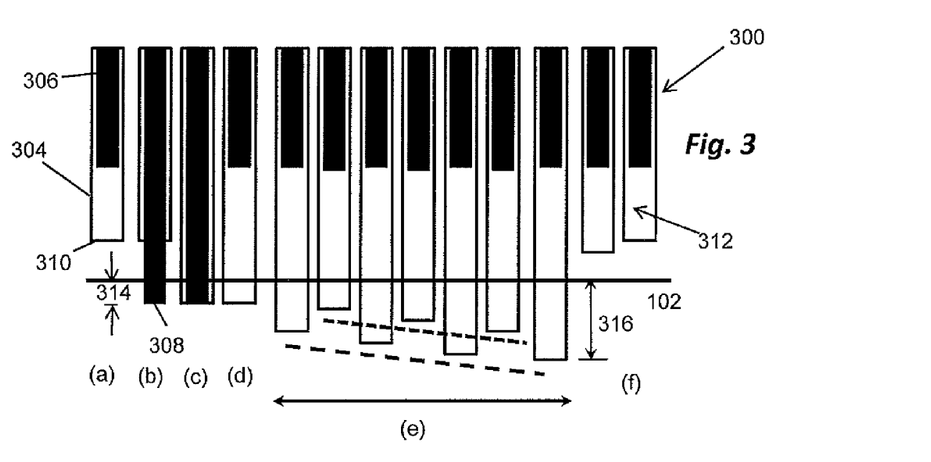
FIG. 3 illustrates the stages of operation of another example of an embodiment of the invention, directed to a pulsed coring or dissecting operation.

FIG. 3 shows a follicular unit removal, harvesting, or dissection according to another embodiment of the method. This technique will be referred to as "pulsed coring." In accordance with one general aspect, the pulsed coring may be implemented with a harvesting cannula comprising a single elongated body, and comprises advancing the harvesting cannula into the body surface in a series of one or more advancing and retracting steps, until the distal end of the harvesting cannula is disposed at a depth in the body surface sufficient to encapsulate a follicular unit. The advancing and retracting steps may be performed in a pulsed manner having a variety of constant and/or varying advancing and retracting increments as described below in reference to FIGS. 3-6. While the embodiments of FIGS. 3-6 are shown and described in reference to the harvesting tool incorporating a first and a second elongated body, similar principles and methods could be applied to a harvesting tool having a single elongated body.

In the alternative mode of operation of FIG. 3, the initial steps may be similar to the steps (a)-(c) described in relation to FIG. 1a above. For example, this may include disposing the removal tool 300 adjacent the body surface 102, advancing the first elongated body 306 to incise a cut in the skin surface, and then in a first stage of an at least two stage process, advancing the second elongated body 304 over the first elongated body 306, such that a distal tip 310 of the second elongated body 304 enters the body surface 102, following the path initiated by the first elongated body 306. It can be seen that, optionally, in step 3(d) the first elongated body 306 is retracted or "blown back." In this embodiment, however, additional steps are taken to prevent compression of the tissue in the vicinity of the follicular unit to be removed. In addition to the optional step 3(d) of "blowing back" as explained in reference to prior embodiments, the second elongated body 304 is pulsed, rather than being advanced in a straightforward manner in the techniques described hereinbefore. In this pulsed motion, identified as step 3(e), the second elongated body 304 is advanced into the body surface 102 by an incremental distance, and retracted back by a lesser increment, before being advanced by the same incremental amount again, and then retracted again, for example, by the same lesser increment. By repeating these steps for several successions, the distal tip 310 of the second elongated body 304 eventually reaches the second depth 316, the depth at which the distal end of the second elongated body 304 encapsulates the follicular unit. Having incised the body tissue surrounding the follicular unit, in step 3(f), the second elongated body 304 is removed from the body surface 102, and may bring the follicular unit up with it, either with or without additional assistance (for example, by use of suction). Alternatively forceps, tweezers, or a similar such device can be used to remove the already dissected follicular unit from the body surface. Although in this particular embodiment, it can be seen that the first elongated body 306 was in fact "blown back" or retracted up and into the second elongated body 304 at the point at which both distal tips 308, 310 were about at the first depth 314, it will be appreciated that the first elongated body 306 may remain in the body 102 surface until the second elongated body 304 has reached a point anywhere between the first and second depths, 314 and 316 respectively, before being blown back or retracted. Alternatively, the pulsed step 3(*e*) may be applied without "blowing back" or retracting the first elongated body 306 at this stage, though the tissue adjacent the follicular unit to be removed will likely be compressed more than in the case where "blowback" step is performed.

Figure 4:
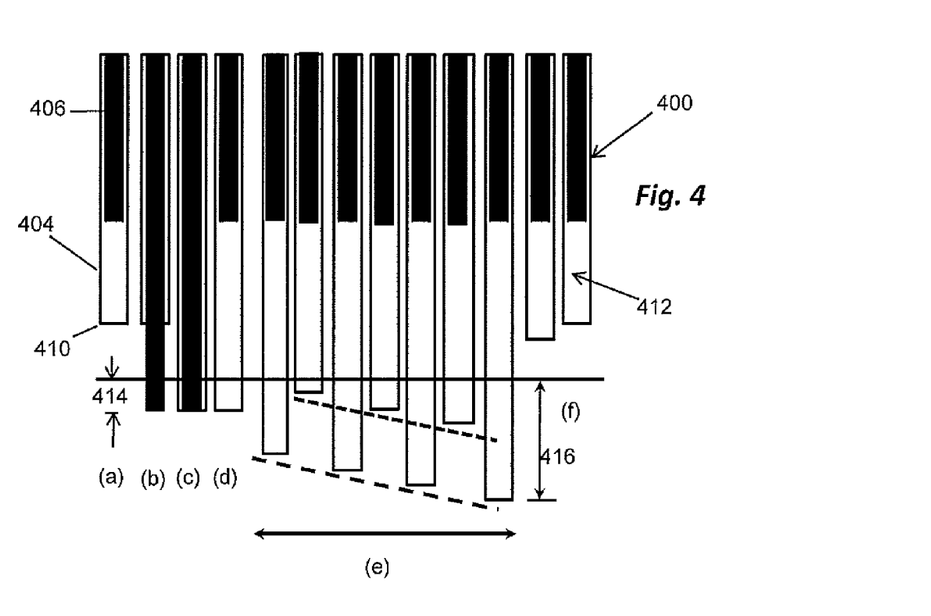
FIG. 4 illustrates the stages of operation of yet another example of an embodiment of the invention, directed to another pulsed coring/dissection.

FIG. 4 illustrates another embodiment of the method in which the steps 4(*a*)-(*d*) and 4(*f*) are similar to those described with reference to FIGS. 3(*a*)-(*d*) and 3(*f*) but provide for variations in the coring pulses. In this particular embodiment, in step 4(*e*), once the first depth 414 has been reached, the second elongated body 404 is further advanced on a first pulse by a first increment. However, rather than being retracted a lesser increment as seen in FIG. 3, the second elongated body 404 is retracted on a first pulse a greater increment than it was initially advanced on that first pulse. In other words, in reference to FIG. 4, the second elongated body 404 may be retracted on the first pulse to a level above the first depth 414 where the pulsing started, therefore creating greater volume into which the tissue can expand and/or decompress. The same process could be repeated on a second and/or subsequent pulses of advancing/retracting steps, however, it is not required. Therefore, in some embodiments, at least during the first pulse the second elongated body is retracted by a greater increment that it was initially advanced on that pulse, and then subsequent to this first pulse, during the second pulse or any further pulse, if present, the advancement and retraction can be conducted, for example, as described in reference to FIG. 3. Many variations of the amount of advancement and retraction of the elongated body 404 are contemplated in reference to various embodiments. For example, the advancement and retraction increments may differ (increase or decrease) on all or any of the pulses.

Figure 5:
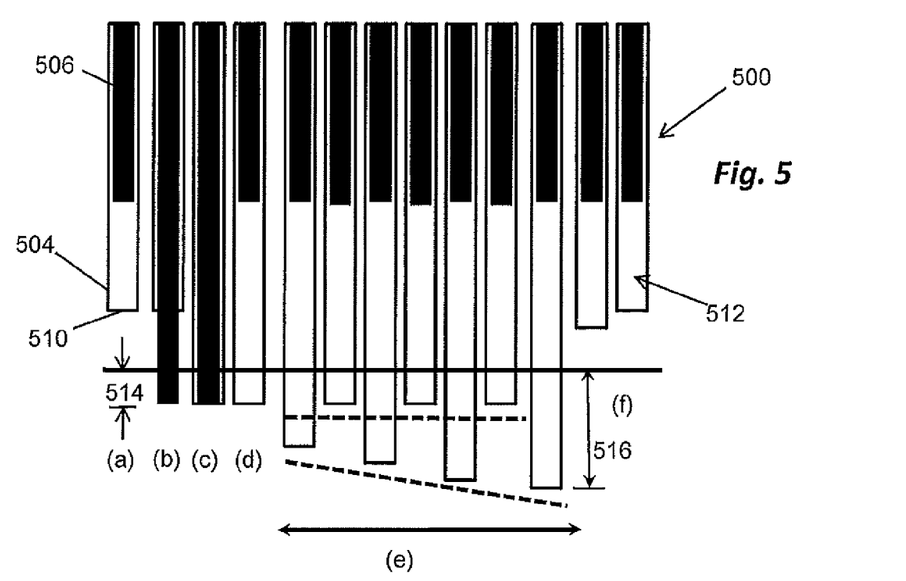
FIG. 5 illustrates the stages of operation of a further example of an embodiment of the invention, directed to an alternative pulsed coring operation.

FIG. 5 illustrates a further embodiment of the method. In this embodiment, once the first depth 514 has been reached, the second elongated body 504 may be advanced by a constant or an increasing/changing increment as it pulses, but always returns to a position that is at the same (for example, pre-set known depth) beneath the surface on the retracting pulse. In the example of FIG. 5, the second elongated body 504 is shown to return during pulsing to the depth 514, however, it other embodiments, it could be any other set depth, for example, the depth below 514, or above 514.

Yet another method of dissecting a follicular unit using a multi-part tool assembly comprising coaxially disposed first and second elongated bodies is provided. The method comprises: advancing a first elongated body relative to a skin surface such that a distal tip of the first elongated body penetrates the skin surface surrounding a follicular unit and initiates a path penetrating to a first depth; advancing the second elongated body relative to the skin surface, such that a relatively duller distal tip of the second elongated body enters the skin surface following the path initiated by the first elongated body and wherein while beneath the skin surface the second elongated body is advanced in a succession of advancing steps. The advancing steps may include advancing the distal tip of the second elongated body to an intermediate depth and maintaining it at the intermediate depth for a predetermined time to allow the follicular unit at least partially recover from its compressed state and then advancing to a second depth at which the follicular unit is substantially dissected.

Figure 6:
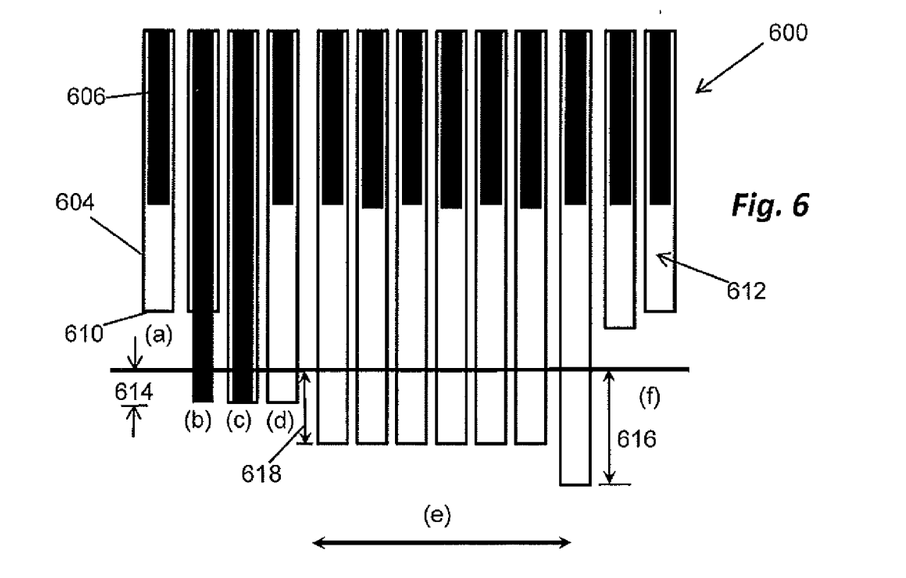
FIG. 6 illustrates the stages of operation of a still further example of another alternative embodiment of the invention.

FIG. 6 illustrates such an embodiment. In this embodiment, once the second elongated body 604 has reached its first depth 614, it is advanced to an intermediate, for example, preset depth 618 between the first and second depths 614 and 616 respectively, before advancing to the second and final depth 616. During the time the second elongated body 604 is at this preset intermediate depth 618, it is preferably paused in terms of depth location, but it may be optionally spun, or rotated, or oscillated, allowing the tissue to have time to decompress, relax, and ultimately release stress. Another advantage of this method/technique of pausing at an intermediate depth is that it allows the second elongated body to continue dissecting the follicular unit during pausing at the intermediate depth while minimizing the chance of follicular unit transection. For example, a combination of the pressure created by the elongated body at the intermediate depth and the spinning, or rotation, or oscillation improves the ability of the elongated body, even with the dull distal tip, to cut through tissue. The length of time that the first elongated body 604 is paused at this intermediate depth 618, may be, between about 1 and 3 seconds, for example, 2 seconds. This time may vary from patient to patient, but should be sufficient to allow the follicular unit to relax from its compressed state. In some embodiments, any of the embodiments with the pulsed coring may be combined with the embodiment of FIG. 6. For example, the harvesting tool may be advanced in a pulsed manner in a succession of one or more alternating advancing or retracting steps, then it could be advanced in several successive advancing steps as described in reference to FIG. 6. Alternatively, the harvesting tool may be first advanced with an intermediate stop as described in reference to FIG. 6, however, the next advancing step does not reach the full desired dissecting depth, and instead the harvesting tool proceeds with several alternating advancement/retraction steps (pulsing steps) to reach the final desired depth of dissection.

It will be appreciated that the variations of depths, pulsing and pausing combinations discussed above, are not exhaustive, and many other variations exist. The methodology applied to the harvesting of follicular units from a patient's skin will depend not only on the configuration of the device and its associated driving technology, but also on the patient, his/her body surface, or the physical nature of the follicular units themselves. One or more of the methodologies may be applied alone or in combination when harvesting follicular units from a patient.

It will be apparent that the number of steps that are utilized for such methods are not limited to those described above. Also, the methods do not require that all the described steps are present. Although the methodology described above as discrete steps, one or more steps may be added, combined or even deleted, without departing from the intended functionality of the embodiments of the invention. The steps can be performed in a different order or have the steps shared between more than one processor, for example. It will also be apparent that the method described above may be performed manually, or they may be partially or substantially automated, including performed using robotic systems.

Although described primarily in association with a removal tool comprising coaxial elongated bodies, the systems and methods described herein may be implemented in the embodiments comprising a harvesting cannula with a single elongated body and a blunt or relatively dull dissecting tip as well. The associated methods may comprise advancing an elongated body relative to a skin surface such that a relatively dull distal tip of the elongated body dissects the follicular unit (for example, by entering a path previously initiated by a separate sharp piercing device) and while beneath the skin surface advancing in a pulsed manner comprising a succession of advancing and retracting steps. In alternative embodiments similar to those described in reference to FIG. 6, the advancement of the elongated body with a dull distal tip while beneath the skin surface may comprise advancement to an intermediate depth and maintaining it at the intermediate depth for a predetermined time to allow the follicular unit at least partially recover from its compressed state and then advancement to a second depth at which the follicular unit is substantially dissected.

As will be appreciated by those skilled in the art, the methods of the present invention may be embodied, at least in part, in digital electronic circuitry, in computer hardware, firmware, software, in software and carried out in a computer system of another data processing system, or in a combination of the aforementioned. Method steps can be performed by special purpose logic circuitry, e.g. an FPGA or an ASIC. Propagated signals or a machine-readable medium may be used to store software and data which causes the system to perform methods of the present invention. The above-mentioned machine-readable medium may include any suitable medium capable of storing and transmitting information in a form accessible by processing device, for example, a computer. Some examples of the machine-readable medium include, but not limited to, magnetic disc storage, flash memory device, optical storage, random access memory, etc. A computer program can be written in any form of programming language, including compiled or interpreted languages, and it can be in a stand-alone program or as a module, component, subroutine, or other such embodiment. Processors suitable for the execution of computer programs include, by way of example, both general and special purpose microprocessors, and any one or more processors of any kind of digital computer.

It will be further appreciated by those skilled in the art that the invention is not limited to the use of a particular system, and that automated (including robotic), semi-automated, and manual systems and apparatus may be used for positioning and actuating the respective removal tools and other devices and components disclosed herein.

The foregoing illustrated and described embodiments of the invention are susceptible to various modifications and alternative forms, and it should be understood that the invention generally, as well as the specific embodiments described herein, are not limited to the particular forms or embodiments disclosed, but to the contrary cover all modifications, equivalents and alternatives falling within the scope of the appended claims. By way of non-limiting example, it will be appreciated by those skilled in the art that particular features or characteristics described in reference to one figure or embodiment may be combined as suitable with features or characteristics described in another figure or embodiment. Applicant regards the subject matter of the invention to include all novel and nonobvious combinations and subcombinations of the various elements, features, functions, and/or properties disclosed herein.

What is claimed is:

1. A method of dissecting an individual follicular unit using a multi-part tool assembly comprising coaxially disposed first and second elongated bodies, the method comprising:

advancing a first elongated body relative to a skin surface such that a distal tip of the first elongated body penetrates the skin surface surrounding a follicular unit and initiates a path;

advancing a second elongated body relative to the skin surface, such that a distal tip of the second elongated body enters the skin surface following the path initiated by the first elongated body;

wherein while beneath the skin surface the second elongated body is incrementally advanced in depth in a pulsed manner resulting in overall advancement beneath the skin to dissect the follicular unit, the pulsed manner comprising a succession of alternating advancing and retracting steps, each advancing step having an advancement distance increment and each retracting step having a retraction distance increment, and wherein the advancement increments and/or the retraction increments during dissection of the follicular unit vary in distance on at least some of the advancing and/or retracting steps;

the method further comprising advancing the second elongated body in at least two consecutive advancing steps such that the second elongated body is paused at a depth location of a first of the at least two consecutive advancing steps for a predetermined time before advancing to a second of the at least two consecutive advancing steps.

2. The method of claim 1, wherein incrementally advancing the second elongated body in the pulsed manner begins after the second elongated body has reached a first depth beneath the skin surface.

3. The method of claim 2, wherein the first depth is at least as deep as a depth that the first elongated body penetrates beneath the skin surface.

4. The method of claim 3, comprising withdrawing the first elongated body when the second elongated body is disposed between the first depth and a second depth at which the follicular unit is substantially encapsulated in a lumen of the second elongated body.

5. The method of claim 3, wherein at least on a first retracting step of the pulsed manner the distal tip of the second elongated body is retracted above the first depth beneath the skin surface.

6. The method of claim 2, further comprising withdrawing the first elongated body after the second elongated body has reached the first depth.

7. The method of claim 1, further comprising withdrawing the first and the second elongated bodies from the skin surface, wherein the follicular unit is disposed in a lumen of the second elongated body and withdrawn from the skin surface with the second elongated body.

8. The method of claim 1, wherein the distal tip of the second elongated body is duller than the distal tip of the first elongated body.

9. The method of claim 1, wherein during the retracting steps, the distal tip of the second elongated body is retracted to a pre-determined constant depth beneath the skin surface.

10. The method of claim 1, further comprising rotating or oscillating the second elongated body while it is being stopped for the predetermined time.

11. The method of claim 1, wherein the distal tip of the second elongated body is angled, and wherein the method comprises rotating or oscillating the angled distal tip of the second elongated body at least during a portion of the advancement of the second elongated body beneath the skin surface.

12. A method of dissecting an individual follicular unit using an apparatus comprising coaxially disposed first and second elongated bodies, the method comprising:

advancing a first elongated body relative to a skin surface such that a distal tip of the first elongated body penetrates the skin surface surrounding a follicular unit and initiates a path;

advancing a second elongated body relative to the skin surface, such that a distal tip of the second elongated body enters the skin surface following the path initiated by the first elongated body;

wherein the second elongated body comprises a bifurcated structure having a primary lumen coaxially disposed with respect to the first elongated body and communicating through an opening with a larger non-coaxial secondary lumen, the method further comprises withdrawing the first elongated body through the primary lumen such that the distal tip of the first elongated body substantially clears the opening between the primary and the secondary lumen of the second elongated body, and directing the follicular unit into the non-coaxial larger secondary lumen of the second elongated body.

13. The method of claim 12, wherein the bifurcated structure comprises a Y-shaped structure comprising the primary lumen and the secondary lumen which diverts at an angle from the primary lumen.

14. The method of claim 12, wherein directing comprises placing the secondary lumen of the second elongated body in communication with a source providing a pressure differential.

15. The method of claim 14, wherein the source provides a pulsed pressure differential, the method further comprising applying varying pressure to remove the follicular unit.

16. The method of claim 12, further comprising incrementally advancing the second elongated body in depth in a pulsed manner comprising a succession of alternating advancing and retracting steps, each advancing step having an advancement distance increment and each retracting step having a retraction distance increment.

17. A method of dissecting a follicular unit using an apparatus comprising coaxially disposed first and second elongated bodies, the method comprising:

advancing a first elongated body relative to a skin surface such that a distal tip of the first elongated body penetrates the skin surface surrounding a follicular unit and initiates a path to a first depth;

advancing a second elongated body relative to the skin surface, such that a distal tip of the second elongated body enters the skin surface following the path initiated by the first elongated body;

wherein while beneath the skin surface the second elongated body is incrementally advanced in depth in a succession of advancing steps, the succession of advancing steps includes advancing the distal tip of the second elongated body to an intermediate depth which is below the first depth, stopping advancement and maintaining the second elongated body at the intermediate depth for a predetermined time to allow the follicular unit to at least partially recover from its compressed state and then continue advancing the second elongated body to a second depth at which the follicular unit is substantially dissected, the second depth being below the intermediate depth.

18. The method of claim 17, wherein advancing the distal end of the first or the second elongated body into the skin surface comprises rotating or oscillating the respective elongated body about its longitudinal axis.

19. The method of claim 17, further comprising placing the lumen of the second elongated body in communication with a source providing a pressure differential.

20. The method of claim 19, further comprising pulsing pressure between an elevated pressure and a less elevated pressure to provide an alternating pressure differential within the lumen of the second elongated body.

21. The method of claim 20, wherein the follicular unit is caused to be elongated during the provision of the elevated pressure and caused to relax during the less elevated pressure.

22. The method of claim 17, wherein the tool assembly is attached to a moveable arm of an automated system.

23. The method of claim 17, wherein the method is implemented at least in part under the control of a computer.

24. The method of claim 17, comprising spinning, rotating or oscillating the second elongated body while it is maintained at the intermediate depth.

25. The method of claim 17, wherein the predetermined time comprises a time range between one and three seconds.

26. The method of claim 17, further comprising incrementally advancing the second elongated body in a pulsed manner, the pulsed manner comprising a succession of alternating advancing and retracting steps.

27. The method of claim 26, wherein the incremental advancing of the second elongated body in the pulsed manner is carried out prior to the incremental advancing in the succession of advancing steps or after reaching the second depth.

28. The method of claim 17, wherein the distal tip of the second elongated body is duller than the distal tip of the first elongated body.

29. The method of claim 17, comprising withdrawing the first elongated body before the second elongated body has reached its final depth of advancement to dissect the follicular unit.

30. The method of claim 17, wherein the succession of consecutive advancing steps has a constant or varying increment.

* * * * *